(12) United States Patent
Hanecak et al.

(10) Patent No.: US 7,067,497 B2
(45) Date of Patent: *Jun. 27, 2006

(54) MODULATION OF TELOMERE LENGTH BY OLIGONUCLEOTIDES HAVING A G-CORE SEQUENCE

(75) Inventors: Ronnie C. Hanecak, San Clemente, CA (US); Kevin P. Anderson, Carlsbad, CA (US); C. Frank Bennett, Carlsbad, CA (US); Ming-Yi Chiang, San Diego, CA (US); Vickie L. Brown-Driver, Solana Beach, CA (US); David J. Ecker, Encinitas, CA (US); Timothy A. Vickers, Oceanside, CA (US); Jacqueline R. Wyatt, Encinitas, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 298 days.

This patent is subject to a terminal disclaimer.

(21) Appl. No.: 10/038,335

(22) Filed: Jan. 2, 2002

(65) Prior Publication Data

US 2003/0096776 A1    May 22, 2003

Related U.S. Application Data

(63) Continuation-in-part of application No. 09/299,058, filed on Apr. 23, 1999, now abandoned, which is a continuation of application No. 08/403,888, filed as application No. PCT/US93/09297 on Sep. 29, 1993, now Pat. No. 5,952,490, which is a continuation-in-part of application No. 07/954,185, filed on Sep. 29, 1992, now abandoned.

(51) Int. Cl.
*C07H 21/04* (2006.01)
*A61K 31/7115* (2006.01)
*A61K 31/712* (2006.01)
*A61K 31/7125* (2006.01)

(52) U.S. Cl. ............. 514/44; 536/23.1; 536/24.5; 536/25.2

(58) Field of Classification Search .......... 536/23.1, 536/24.5, 25.2; 514/44
See application file for complete search history.

(56) References Cited

U.S. PATENT DOCUMENTS 5,489,508 A * 2/1996 West et al. .............. 435/6

| 5,523,389 | A | * | 6/1996 | Ecker et al. ............... 536/23.1 |
| 5,633,360 | A | * | 5/1997 | Bischofberger et al. ... 536/22.1 |
| 5,837,857 | A | | 11/1998 | Villeponteau et al. ... 536/24.31 |
| 5,929,226 | A | * | 7/1999 | Padmapriya et al. ....... 536/25.3 |
| 5,952,490 | A | * | 9/1999 | Hanecak et al. ........... 536/24.5 |
| 5,958,680 | A | | 9/1999 | Villeponteau et al. ......... 435/6 |

FOREIGN PATENT DOCUMENTS

| WO | WO 95/13382 | 5/1995 |
| WO | WO 96/01614 | 1/1996 |
| WO | WO 96/01835 | 1/1996 |
| WO | WO 97/38013 | 10/1997 |

OTHER PUBLICATIONS

Nature Biotechnology, 1997, vol. 15, pp. 519-524.*
Branch, TIBS, 1998, vol. 23, pp. 45-50.*
DeMagalhaes et al., Rejuvenation Research, 2004, vol. 7, No. 2, pp. 126-133.*
Counter, C., et al., "Telomere shortening associated with chromosome instability is arrested in immortal cells which express telomerase activity," *The EMBO J.*, 1992, 11(5), 1921-1929.
Far, et al., "Functional reintroduction of human telomeres into mamalian cells," *PNAS USA*, 1992, 88, 7006-7010.
Greider, C., "Telomeres," *Current Opinion in Cell Biology*, 1991, 3, 444-451.
Harley, C., et al., "Telomeres shorten during ageing of human fibroblasts," *Nature*, 1990, 345, 458-460.
Hastie, N.D., et al., "Telomore reduction in human colorectal carcinoma and with ageing," *Nature*, 1990, 346, 866-868.
Herbert, B.S., et al., "Inhibition of human telomerase in immortal human cells leads to progressive telomere shortening and cell death," *PNAS*, Dec. 7, 1999, 96(25), 14276-14281.
Norton, J.C., et al., "Inhibition of human telomerase activity by peptide nucleic acids," *Nature Biotechnology*, May 1996, 14, 615-619.

(Continued)

Primary Examiner—David Guzo
(74) Attorney, Agent, or Firm—ISIS Patent Department; Cozen O'Connor, P.C.

(57) ABSTRACT

Modified oligonucleotides having a GGG motif sequence and a sufficient number of flanking nucleotides to modulate the telomere length of a chromosome are provided. Methods of modulating telomere length of a mammalian chromosome in vitro and in vivo are also provided, as are methods for inhibiting the division of a malignant mammalian cell and for modulating the effects of cellular aging.

16 Claims, No Drawings

OTHER PUBLICATIONS

Williamson, J.R., "Guanine quartets," *Current Opinion in Structural Biology,* 1993, 3, 357-362.

Zahler, A.M., et al., "Inhibition of telomerase by G-quartet DNA structures," *Nature,* Apr. 25, 1991, 350, 718-720.

* cited by examiner

MODULATION OF TELOMERE LENGTH BY OLIGONUCLEOTIDES HAVING A G-CORE SEQUENCE

CROSS-REFERENCE TO RELATED APPLICATIONS

The present application is a continuation-in-part of U.S. application Ser. No. 09/299,058, filed Apr. 23, 1999, now abandoned which is a continuation of U.S. application Ser. No. 08/403,888 filed Jun. 12, 1995, which is U.S. Pat. No. 5,952,490, the U.S. national phase of PCT Application Ser. No. PCT/US93/09297 filed Sep. 29, 1993, which is a continuation-in-part of U.S. application Ser. No. 07/954,185 filed Sep. 29, 1992, now abandoned, each of which is incorporated herein by reference in its entirety.

FIELD OF THE INVENTION

This invention relates to the design and synthesis of oligonucleotides which can be used to modulate telomere length in vivo or in vitro. These compounds can be used prophylactically or therapeutically for diseases associated with abnormal telomere length, such as aging and hyperproliferative conditions, e.g., cancer. Methods for the treatment of cancer and to retard aging are also contemplated by this invention.

BACKGROUND OF THE INVENTION

Modulation of Telomere Length

It has been recognized that telomeres, long chains of repeated nucleotides located at the tip of each chromosome, play a role in the protection and organization of the chromosome. In human cells, the sequence TTAGGG is repeated hundreds to thousands of times at both ends of every chromosome, depending on cell type and age. Harley, C. B. et al., *Nature*, 1990, 345, 458–460; Hastie, N. D. et al., *Nature*, 1990, 346, 866–868. Telomeres also appear to have a role in cell aging which has broad implications for the study of aging and cell immortality that is manifested by cancerous cells.

Researchers have determined that telomere length is reduced whenever a cell divides and it has been suggested that telomere length controls the number of divisions before a cell's innate lifespan is spent. Harley, C. B. et al., *Nature*, 1990, 345, 458–460; Hastie, N. D. et al., *Nature*, 1990, 346, 866–868. For example, normal human cells divide between 70–100 times and appear to lose about 50 nucleotides of their telomeres with each division. Some researchers have suggested that there is a strong correlation between telomere length and the aging of the entire human being. Greider, C. W., *Curr. Opinion Cell Biol.*, 1991, 3, 444–451. Other studies have shown that telomeres undergo a dramatic transformation during the genesis and progression of cancer. Hastie, N. D. et al., *Nature* 1990, 346, 866–868. For example, it has been reported that when a cell becomes malignant, the telomeres become shortened with each cell division. Hastie, N. D. et al., *Nature* 1990, 346, 866–868. Experiments by Greider and Bacchetti and their colleagues have shown that at a very advanced and aggressive stage of tumor development, telomere shrinking may cease or even reverse. Counter, C. M. et al., *EMBO J.* 1992, 11, 1921–1929. It has been suggested, therefore, that telomere blockers may be useful for cancer therapy. In vitro studies have also shown that telomere length can be altered by electroporation of linearized vector containing human chromosome fragments into hybrid human-hamster cell lines. Chromosome fragments consisted of approximately 500 base pairs of the human telomeric repeat sequence TTAGGG and related variants such as TTGGGG, along with adjacent GC-rich repetitive sequences. Farr, C. et al., *Proc. Natl. Acad. Sci. USA* 1992, 88, 7006–7010. While this research suggests that telomere length affects cell division, no effective method for control of the aging process or cancer has been discovered. Therefore, there is an unmet need to identify effective modulators of telomere length.

Guanosine nucleotides, both as mononucleotides and in oligonucleotides or polynucleotides, are able to form arrays known as guanine quartets or G-quartets. For review, see Williamson, J. R., (1993) Curr. Opin. Struct. Biol. 3:357–362. G-quartets have been known for years, although interest has increased in the past several years because of their possible role in telomere structure and function.

In addition to their natural role (in telomeres, for example, though there may be others), oligonucleotides which have a GGGG motif or one or more GGG motifs are useful for inhibiting viral gene expression and viral growth and for inhibiting $PLA_2$ enzyme activity and have long been believed to be useful as modulators of telomere length. Chemical modification of the oligonucleotides for such use is desirable and, in some cases, necessary for maximum activity.

It has now been clearly demonstrated both in vitro and in vivo that oligonucleotides containing a GGG motif are capable of modulating telomere length on mammalian chromosomes. Herbert et al., 1999, Proceedings Natl. Acad. Sci., USA, 96, 14276–14281.

SUMMARY OF THE INVENTION

It has been discovered that oligonucleotides containing at least one GGG motif are effective inhibitors of telomere length on chromosomes.

The formula for an active sequence is generally $(N_XG_{3-4})_QN_X$ wherein X is 1–8 and Q is 1–6. The sequence $(N_XG_4N_Y)_Q$ or $(G_{3-4}N_XG_{3-4})_Q$ wherein X and Y are 1–8, and Q is 1–4 is also believed to be useful in some embodiments of the invention. Compositions and methods for modulating, preferably shortening, telomere length are provided. Preferably the telomeres are mammalian telomeres, i.e., found on mammalian chromosomes, and more preferably are human telomeres. Methods of modulating mammalian telomere length are also provided, as are methods for inhibiting the division of a malignant mammalian cell and for modulating cellular aging.

DETAILED DESCRIPTION OF PREFERRED EMBODIMENTS

It has been discovered that oligonucleotides containing one or more GGG motifs, or G-cores, wherein G is a guanine-containing nucleotide or analog, are effective inhibitors of telomere length on chromosomes. Although the GGG core sequence(s) or G pharmacophore is necessary, sequences flanking the GGG sequence have been found to play an important role in inhibitory activity because it has been found that activity can be modulated by substituting or deleting the surrounding sequences. In the context of this invention, the term "modulate" means to increase or decrease.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates thionoalkylphosphotriesters, selenophosphates and boranophosphates having normal 3'–5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'—most internucleotide linkage i.e., a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference in its entirety.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference in its entirety.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference in its entirety. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester backbone is represented as —O—P—O—$CH_2$—) of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O((CH$_2$)$_n$O)$_m$CH$_3$, O(CH$_2$)$_n$OCH$_3$, O(CH$_{2n}$NH$_2$, O(CH$_2$)$_n$CH$_3$, O(CH$_2$)$_n$ONH$_2$, and O(CH$_2$)$_n$ON((CH$_2$)$_n$CH$_3$))$_2$, where n and m are from 1 to about 10. Other preferred oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$, also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methylene (—CH$_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$—CH═CH$_2$), 2'-O-allyl (2'-O—CH$_2$—CH═CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-b)(1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference in its entirety, and U.S. Pat. No. 5,750,692, which is commonly owned with the instant application and also herein incorporated by reference in its entirety.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992, the entire disclosure of which is incorporated herein by reference in its entirety. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference in its entirety.

It is not necessary for all positions in a given compound to be uniformly modified, and in fact more than one of the aforementioned modifications may be incorporated in a single compound or even at a single nucleoside within an oligonucleotide. The present invention also includes oligonucleotides which are chimeric compounds. "Chimeric" oligonucleotides or "chimeras," in the context of this invention, are oligonucleotides which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligonucleotides of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The oligonucleotides in accordance with this invention preferably comprise from about 6 to about 27 nucleic acid base units. It is preferred that such oligonucleotides have from about 6 to 24 nucleic acid base units. As will be appreciated, a nucleic acid base unit is a base-sugar combination suitably bound to adjacent nucleic acid base unit through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer. It is also well known to use similar techniques to prepare other oligonucleotides such as the phosphorothioates and alkylated derivatives.

The essential feature of the invention is a conserved $G_3$ or $G_4$ core sequence and a sufficient number of additional flanking bases to significantly inhibit activity. It has also been discovered that chemical modifications are tolerated in the oligonucleotide. For example, phosphorothioate and 2'-O-methyl modifications have been incorporated.

The formula for an active sequence is: 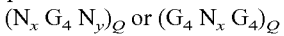
wherein X is 1–8 and Q is 1–6.

In some embodiments of the present invention, the sequence $(N_x\ G_4\ N_y)_Q$ or $(G_4\ N_x\ G_4)_Q$ where G=a guanine-containing nucleotide or analog,
N=any nucleotide,
X=1–8,
Y=1–8,
and Q=1–4 is believed to be active.

Modulation of Telomere Length

Oligonucleotides capable of modulating telomere length are contemplated by this invention. In human cells, the sequence TTAGGG is repeated from hundreds to thousands of times at both ends of every chromosome, depending on cell type and age. It is believed that oligonucleotides having a sequence $(N_XG_{3-4})_QN_X$ wherein X is 1–8 and Q is 1–6 would be useful for modulating telomere length.

Since telomeres appear to have a role in cell aging, i.e., telomere length decreases with each cell division, it is believed that such oligonucleotides would be useful for modulating the cell's aging process. Altered telomeres are also found in cancerous cells; it is therefore also believed that such oligonucleotides would be useful for controlling malignant cell growth. Therefore, modulation of telomere length using oligonucleotides of the present invention could prove useful for the treatment of cancer or in controlling the aging process.

It has now been demonstrated that oligonucleotides having a sequence $(N_XG_{3-4})_QN_X$ wherein X is 1–8 and Q is 1–6 are able to modulate telomere length. Herbert et al. (Herbert et al., *Proc. Natl. Acad. Sci. USA*, 1999, 96, 14276–14281) have demonstrated telomere shortening in human mammary epithelial (HME) cells and prostate tumor-derived DU145 cells treated with a 2'-O-methyl chimeric oligonucleotide having the sequence CAGUUAGGGUUAG (SEQ ID NO:1). Telomere length was reduced from 2000 to 1700 base pairs in HME cells (60 day treatment) and from 3600 base pairs to 2200 base pairs in DU145 cells (76 day treatment). Treatment of DU145 cells with a peptide nucleic acid of the sequence Gly-CAGTTAGGGTTAG-Lys (SEQ ID NO:2 with a glycine residue covalently attached to the N-terminus and a lysine residue covalently attached to the C-terminus) caused similar telomere shortening to that caused by the 2'-O-methyl oligonucleotide.

Telomere shortening has also been demonstrated in mice treated with an 2'-O-methyl oligonucleotide, ISIS 24691, having the sequence CAGTTAGGGTTAG (SEQ ID NO:2) and a 2'O-methyl sugar modification at every position and a phosphorothioate backbone throughout.

The following examples are provided for illustrative purposes only and are not intended to limit the invention.

EXAMPLES

Example 1

Oligonucleotide Synthesis

Oligonucleotides may be purchased commercially or synthesized as follows. DNA synthesizer reagents, controlled-pore glass (CPG)-bound and B-cyanoethyldiisopropylphosphoramidites were purchased from Applied Biosystems (Foster City, Calif.). 2'-O-Methyl B-cyanoethyldiisopropylphosphoramidites were purchased from Chemgenes (Needham, Mass.). Phenoxyacetyl-protected phosphoramadites for RNA synthesis were purchased from BioGenex (Hayward, Calif.).

Oligonucleotides were synthesized on an automated DNA synthesizer (Applied Biosystems model 380B). 2'-O-Methyl oligonucleotides were synthesized using the standard cycle for unmodified oligonucleotides, except the wait step after pulse delivery of tetrazole and base was increased to 360 seconds. The 3' base bound to the CPG used to start the synthesis was a 2'deoxyribonucleotide. After cleavage from the CPG column and deblocking in concentrated ammonium hydroxide at 55° C. (18 hours), the oligonucleotides were purified by precipitation two times out of 0.5 M NaCl solution with 2.5 volumes ethanol. Analytical gel electrophoresis was accomplished in 20% acrylamide, 8 M urea, 45 mM Tris-borate buffer, pH=7.0. Oligonucleotides were judged from polyacrylamide gel electrophoresis to be greater than 85% full length material.

Example 2

Modulation of Telomere Length by $G_4$ Phosphorothioate Oligonucleotides

The amount and length of telomeric DNA in human fibroblasts has been shown to decrease during aging as a function of serial passage in vitro. To examine the effect of $G_4$ phosphorothioate oligonucleotides on this process, human skin biopsy fibroblasts are grown as described in Harley, C. B., *Meth. Molec. Biol.* 1990, 5, 25–32. Cells are treated with the oligonucleotides shown in Table 1, by adding the oligonucleotide to the medium to give a final concentration of 1 μM, 3 μM or 10 μM; control cells receive no oligonucleotide. Population doublings are counted and DNA is isolated at regular intervals. Telomere length is determined by Southern blot analysis and plotted against number of population doublings as described in Harley, C. B. et al., *Nature* 1990, 345, 458–460. The slope of the resulting linear regression lines indicates a loss of approximately 50 bp of telomere DNA per mean population doubling in untreated fibroblasts. Harley, C. B. et al., *Nature* 1990, 345, 458–460. Treatment with oligonucleotides of Table 1 is expected to result in modulation of telomere length.

TABLE 1

Effect of $G_4$ Phosphorothioate Oligonucleotides on Telomere Length in Aging Fibroblasts

| ISIS NO. | SEQUENCE | SEQ ID NO: |
|---|---|---|
|  | TT AGGG |  |
| 5739 | TT GGGG |  |
| 5756 | TT AGGG TT |  |
| 5320 | TT GGGG TT |  |
| 5675 | TT GGGG TT GGGG TT | 3 |
| 5651 | TT GGGG TT GGGG TT GGGG TT | 4 |
|  | GGGG |  |
|  | TTTT GGGG |  |
|  | TTTA GGGG |  |
| 5673 | GGGG |  |

Example 3

Chimeric 2'-O-methyl $G_4$ Oligonucleotides with Deoxy Gaps

A series of phosphorothioate oligonucleotides were synthesized having a 2'-O-methyl substitution on the sugar of each nucleotide in the flanking regions, and 2'-deoxynucleotides in the center portion of the oligonucleotide (referred to as the "deoxy gap"). Deoxy gaps varied from zero to seven nucleotides in length. Additional chimeric oligonucleotides were synthesized having the sequences GTTG-GAGACCGGGGTTGGGG (SEQ ID NO:5) and CACGGGGTCGCCGATGAACC (SEQ ID NO:6). These oligonucleotides were 2'-O-methyl oligonucleotides with deoxy gaps as described above, but instead of a uniform phosphorothioate backbone, these compounds had phosphorothioate internucleotide linkages in the deoxy gap region and phosphodiester linkages in the flanking region.

Additional oligonucleotides were synthesized with 2'-O-propyl modifications. 2'-O-propyl oligonucleotides were prepared from 2'-deoxy-2'-O-propyl ribosides of nucleic acid bases A, G, U(T), and C which were prepared by modifications of literature procedures described by B. S. Sproat, et al., *Nucleic Acids Research* 18:41–49 (1990) and H. Inoue, et al., *Nucleic Acids Research* 15:6131–6148 (1987). ISIS 7114 is a phosphorothioate which has SEQ ID NO:6, and has a 2'-O-propyl modification on each sugar. ISIS 7171 is a phosphorothioate gapped 2'-O-propyl oligonucleotide with the same sequence, and 2'-O-propyl modifications at positions 1–7 and 14–20 (6-deoxy gap).

Example 4

Cell Lines

Cell lines were produced and grown as described in Herbert et al., 1999, *Proc. Natl. Acad. Sci. USA*, 96, 14276–14281. Briefly, spontaneously immortalized human mammary epithelial (HME) cells were grown in supplemented serum-free medium and used between population doublings 100 and 150. Prostate tumor-derived DU145 cells were maintained in DMEM containing fetal calf serum and antibiotics.

Example 5

Oligonucleotides

The oligonucleotides are fully described in Herbert et al., 1999, *Proc. Natl. Acad. Sci. USA*, 96, 14276–14281. 2'-O-methyl oligonucleotides were purchased from Oligos Etc. and Oligo Therapeutics (Wilsonville Oreg.). The "match" phosphorothioate modified 2'-O-methyl RNA oligonucleotide has the sequence CAGUUAGGGUUAG (SEQ ID NO:1) wherein the bold nucleotides have phosphorothioate linkages. The mismatch 2'-O-methyl oligonucleotide is CAGUUAGAAUUAG (SEQ ID NO:7). Match and mismatch PNAs were synthesized automatically with a PerSeptive Biosystems (Framingham Mass.) Expedite 8909 Synthesizer using Fmoc protocols and reagents obtained from PE Biosystems. PNAs were purified by HPLC and characterized by matrix-assisted laser desorption time-of-flight mass spectrometry. The match PNA has the sequence Gly-CAGTTAGGGTTAG-Lys (SEQ ID NO:2 with a glycine residue covalently attached to the N-terminus and a lysine residue covalently attached to the C-terminus); the mismatch is Gly-CAGTTAGAATTAG-Lys (SEQ ID NO:8 with a glycine residue covalently attached to the N-terminus and a lysine residue covalently attached to the C-terminus). DNA oligonucleotides used for transfection of PNA/DNA complexes were obtained from Life Technologies (Gaithersburg, Md.). The DNA oligonucleotide complexed to the match PNA has the sequence TCTAACCCTAA (SEQ ID NO:9); the DNA oligonucleotide complexed to the mismatch PNA has the sequence TCTAATTCTAA (SEQ ID NO:10).

Example 6

Transfection of Cells with Oligonucleotides

Cells were transfected as described in Herbert et al., 1999, *Proc. Natl. Acad. Sci. USA*, 96, 14276–14281. Briefly, HME cells were transfected with 2'-O-methyl RNA and mismatch control oligonucleotides using the FuGENE6 Transfection Reagent protocol (Roche Molecular Biochemicals). DU145 cells were plated at 25,000 cells per well in a 24 well plate. For DNA/PNA transfections, 100 μM PNA was hybridized with 109 μM of the appropriate DNA oligonucleotide in 0.5× PBS. Cells were allowed to adhere and transfected with 2.0 μl (7 μg/ml) of Lipofectamine (Life Technologies) and 0.5 μM 2'-O-methyl RNA oligonucleotide or 1 μM PNA/DNA complex in 200 μl total Opti-MEM (Life Technologies) according to the manufacturer's instructions. Cells were transfected with oligonucleotides at 3 to 4 day intervals for 120 days.

Example 7

Measurement of Reduction of Telomere Length in Cell Culture by Oligonucleotide Treatment Telomere length was measured as described by Herbert et al., 1999, *Proc. Natl. Acad. Sci. USA*, 96, 14276–14281. Briefly, mean telomere length was evaluated by using telomere restriction fragment analysis, a variation of standard Southern analysis, and was quantitated as described by Shay et al., 1994, *Methods Mol. Genet.*, 5, 263–268. Digested samples were resolved on a 0.7% agarose gel and hybridized to a telomeric probe (($^{32}$P)(TTAGGG)$_4$ (SEQ ID NO: 11) oligonucleotide).

Within 60 days of treatment, the mean telomere length of HME-50 cells treated with the 2'-O-methyl RNA G-core oligonucleotide of sequence CAGUUAGGGUUAG (SEQ ID NO:1) was reduced from 2000 to 1700 base pairs. This decrease in measured telomere restriction fragment length may be an underestimate of the total loss of telomere length because little telomeric DNA remained to hybridize with the labeled probe. The telomere restriction fragment length of cells treated with the mismatch 2'-O-methyl RNA oligonucleotide lacking the GGG sequence was unchanged at 2000 base pairs.

DU145 cells have longer telomeres than HME-50 cells. In DU145 cells treated with the 2'-O-methyl G-core oligonucleotide of sequence CAGUUAGGGUUAG (SEQ ID NO:1) for 76 days, the mean telomere restriction fragment length decreased from 3600 base pairs to 2200 base pairs. Again the signal was greatly reduced due to reduction in telomere repeat number.

A PNA oligonucleotide of sequence Gly-CAGTTAGGGTTAG-Lys (SEQ ID NO:2 with an amino acid residue tethered to each end) caused telomere shortening in DU145 cells similar to that caused by the 2'-O-methyl oligonucleotide.

The above-described results are shown in FIG. 4 of Herbert et al., 1999, *Proc. Natl. Acad. Sci. USA*, 96, 14276–14281.

Example 8

Measurement of Reduction of Telomere Length in vivo by Oligonucleotide Treatment DU145 xenografts were implanted in seven nude mice. Mice were injected on bilateral flanks with 3 million DU145 cells. Once tumors reached 100–500 mm$^3$, mice were injected intraperitoneally with either PBS (control) or ISIS 24691 antisense oligonucleotide. Mice 1–3 were controls, mice 4–7 were treated long-term with 2'-O-methyl oligonucleotide ISIS 24691 CAGTTAGGGTTAG; SEQ ID NO:2). This oligonucleotide has a 2'-O-methyl sugar modification at every position and a phosphorothioate backbone throughout. The C residue is a 5-methyl C residue.

The results are shown in Table 2.

TABLE 2

| Mouse | Approximate Telomere length (bp) | Treatment |
|---|---|---|
| 1 | 4400 | Control |
| 2 | 3900 | Control |
| 3 | 3900 | Control |
| 4 | 2200 | ISIS 24691 |
| 5 | 2800 | ISIS 24691 |

TABLE 2-continued

| Mouse | Approximate Telomere length (bp) | Treatment |
|---|---|---|
| 6 | 3000 | ISIS 24691 |
| 7 | 3800 | ISIS 24691 |

As shown in the table, the average telomere length was approximately 4067 for control mice and 2950 for oligonucleotide treated mice, a reduction in telomere length of 27.5% after oligonucleotide treatment.

What is claimed is:

1. A method for inhibiting the division of a malignant mammalian cell comprising contacting said malignant mammalian cell with a chemically modified oligonucleotide having no more than about 27 nucleic acid base units, said oligonucleotide having the sequence $(N_xG_{3-4})_QN_X$ wherein X is 1 to 8 and Q is 1 to 6, wherein said oligonucleotide modulates mammalian telomere length.

2. The method of claim 1 which is carried out in vitro.

3. The method of claim 1 which is carried out in vivo.

4. A chemically modified oligonucleotide having no more than about 27 nucleic acid base units, said oligonucleotide having the sequence $(N_xG_4)_QN_X$ wherein X is 1 to 8 and Q is 1 to 6.

5. The oligonucleotide of claim 4 which has at least one phosphorothioute linkage.

6. The oligonucleotide of claim 4 which has at least one 2' modification of a sugar of said oligonucleotide.

7. The oligonucleotide of claim 4 which is a chimeric oligonucleotide.

8. The otigonucleotide of claim 4 wherein said chemical modification is:
- a backbone modification selected from the group consisting of chiral phosphorothioate, phosphorodithioate, phosphotriester, aminoalkylphosphotriester, methyl phosphonate, 3'-alkylene phosphonate, 5'-alkylene phosphonate, chiral phosphonate, phosphinate, phosphoramidate, thionoalkyiphosphonate, thionoalkylphosphotriester, selenophosphate, boranophosphate, morpholino, siloxane, sulfide, sulfoxide, sulfone, formacetyl, thioformacetyl, methylene formacetyl, thioformacetyl, riboacetyl, alkene containing backbone, sulfamate, methyleneimino, methylenehydrazino, sulfonate, sulfonamide, and amide; or
- a modified 2' sugar moiety selected from the group consisting of F, N-alkyl, O-alkenyl, S-alkenyl, N-alkenyl, O-alkynyl, S-alkynyl, N-alkynyl, O-alkyl-O-alkyl, $C_1$ to $C_{10}$ lower alkyl, substituted lower alkyl, alkenyl, alkynyl, alkaryl, aralkyl, O-alkaryl, O-aralkyl, SH, $SCH_3$, OCN, Cl, Br, CN, $CF_3$, $OCF_3$, $SOCH_3$, $SO_2CH$, $ONO_2$, $NO_2$, $N_3$, $NH_2$, heterocycloalkyl, heterocycloalkaryl, aminoalkylamino, polyalkylamino, and substituted silyl, wherein the alkyl, alkenyl and alkynyl may be substituted or unsubstituted $C_1$ to $C_{10}$ alkyl or $C_2$ to $C_{10}$ alkenyl and alkynyl; or
- a modified nucleobases selected from the group consisting of 5-methylcytosine, 5-hydroxymethyl cytosine, xanthine, hypoxanthine, 2-aminoadenine, 6-methyl adenine, 6-methyl guanine, 2-propyl adenine, 2-propyl guanine, 2-thiouracil, 2-thiothymine, 2-thiocytosine, 5-halouracil, 5-holocytosine, 5-propynyl uracil, 5-propynyl cytosine, 6azo uracil, 6-azo cytosine, 6-azo thymine, 5-uracil, 4-thiouracil, 8-halo guanine, 8-amino guanine, 8-thiol guanine, 8-thioalkyl guanine, 8-hydroxyl guanine, 8-halo adenine, 8-amino adenine, 8-thiol adenine, 8-thioalkyl adenine, 8-hydroxyl adenine, 5-halo uracil, 5-bromo uracil, 5-trifluoromethyl uracil, 5-halo cytosine, 5-bromo cytosine, 5-trifluoromethyl cytosine, 7-methylguanine, 7-methyladenine, 2-F-adenine, 2-amino-adenine, 8-azaguanine, 8-azaadenine, 7-deazaguanine, 7-deazaudenine, 3-deazaguanine, 3-deazeadenine, phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), substituted phenoxazine cytidine (e.g. 9-(2-aminoethoxy)-H-pyrimido(5,4-b)(1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one), 7-deaza-adenine, 7-deazaguanosine, 2-amninopyridine, and 2-pyridone.

9. The oligonucleotide of claim 4 wherein said oligonucleotide modulates mammalian telomere length.

10. The oligonucleotide of claim 8 wherein the 2' sugar modification is —O—$CH_2CH_2OCH_3$, —$O(CH_2ON(CH_3)_2$, —O—$CH_2$—O—$CH_2$—$N(CH_2)_2$, —O—$CH_3$, —$OCH_2CH_2NH_2$, —$CH_2CH=CH_2$), —F, —$O((CH_2)_nO)_mCH_3$, —$O(CH_2)_nOCH_3$, —$O(CH_2)_n$ $NH_2$, —$O(CH_2)_nCH_3$, —$O(CH_2)_nONH_2$, or —$O(CH_2)_nON((CH_2)_nCH_3)_2$, where n and m are from 1 to about 10.

11. A chemically modified oligonucleotide having no more than about 27 nucleic acid base units, said oligonucleotide having the sequence $(N_xG_4N_y)_Q$ or $(G_4N_xG_4)_Q$ wherein X is 1 to 8, Y is 1 to 8, and Q is 1 to 4, wherein said oligonucleotide modulates mammalian telomere length.

12. The oligonucleotide of claim 11 which has at least one phosphorothioate linkage.

13. The oligonucleotide of claim 11 which has at least one $_2$' modification of a sugar of said oligonucleotide.

14. The oligonucleotide of claim 11 which is a chimeric oligonucleotide.

15. The otigonucleotide of claim 4 wherein said chemical modification is:
- a backbone modification selected from the group consisting of chiral phosphorothioate, phosphorodithioate, phosphotriester, aminoalkylphosphotriester, methyl phosphonate, 3'-alkylene phosphonate, 5'-alkylene phosphonate, chiral phosphonate, phosphinate, phosphoramidate, thionoalkyiphosphonate, thionoalkylphosphotriester, selenophosphate, boranophosphate, morpholino, siloxane, sulfide, sulfoxide, sulfone, formacetyl, thioformacetyl, methylene formacetyl, thioformacetyl, riboacetyl, alkene containing backbone, sulfamate, methyleneimino, methylenehydrazino, sulfonate, sulfonamide, and amide; or
- a modified 2' sugar moiety selected from the group consisting of F, N-alkyl, O-alkenyl, S-alkenyl, N-alkenyl, O-alkynyl, S-alkynyl, N-alkynyl, O-alkyl-O-alkyl, $C_1$ to $C_{10}$ lower alkyl, substituted lower alkyl, alkenyl, alkynyl, alkaryl, aralkyl, O-alkaryl, O-aralkyl, SH, $SCH_3$, OCN, Cl, Br, CN, $CF_3$, $OCF_3$, $SOCH_3$, $SO_2CH$, $ONO_2$, $NO_2$, $N_3$, $NH_2$, heterocycloalkyl, heterocycloalkaryl, aminoalkylamino, polyalkylamino, and substituted silyl, wherein the alkyl, alkenyl and alkynyl may be substituted or unsubstituted $C_1$ to $C_{10}$ alkyl or $C_2$ to $C_{10}$ alkenyl and alkynyl; or
- a modified nucleobases selected from the group consisting of 5-methylcytosine, 5-hydroxymethyl cytosine, xanthine, hypoxanthine, 2-aminoadenine, 6-methyl adenine, 6-methyl guanine, 2-propyl adenine, 2-propyl guanine, 2-thiouracil, 2-thiothymine, 2-thiocytosine, 5-halouracil, 5-holocytosine, 5-propynyl uracil, 5-propynyl cytosine, 6azo uracil, 6-azo cytosine, 6-azo thymine, 5-uracil, 4-thiouracil, 8-halo guanine, 8-amino guanine, 8-thiol guanine, 8-thioalkyl guanine, 8-hydroxyl guanine, 8-halo adenine, 8-amino adenine, 8-thiol adenine, 8-thioalkyl adenine, 8-hydroxyl adenine, 5-halo uracil, 5-bromo uracil, 5-trifluoromethyl uracil, 5-halo cytosine, 5-bromo cytosine, 5-trifluoromethyl cytosine, 7-methylguanine, 7-methyladenine, 2-F-adenine, 2-amino-adenine, 8-azaguanine, 8-azaadenine, 7-deazaguanine, 7-deazaudenine, 3-deazaguanine, 3-deazeadenine, phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), substituted phenoxazine cytidine (e.g. 9-(2-aminoethoxy)-H-pyrimido(5,4-b)(1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one), 7-deaza-adenine, 7-deazaguanosine, 2-amninopyridine, and 2-pyridone.

16. The oligonucleotide of claim 15 wherein the 2' sugar modification is —O—$CH_2CH_2OCH_3$, —$O(CH_2)_2ON(CH_3)_2$, —O—$CH_2$—O—$CH_2$—$N(CH_2)_2$, —O—$CH_3$, —$OCH_2CH_2CH_2NH_2$, —$CH_2$—$CH=CH_2$), —F, —$O((CH_2)_nO)_mCH_3$, —$O(CH_2)_nOCH_3$, —$O(CH_2)_nNH_2$, —$O(CH_2)_nCH_3$, —$O(CH_2)_nONH_2$, or —$O(CH_2)_nON((CH_2)_nCH_3)_2$, where n and m are from 1 to about 10.

* * * * *

UNITED STATES PATENT AND TRADEMARK OFFICE
CERTIFICATE OF CORRECTION

PATENT NO. : 7,067,497 B2
APPLICATION NO. : 10/038335
DATED : June 27, 2006
INVENTOR(S) : C. Frank Bennett et al.

It is certified that error appears in the above-identified patent and that said Letters Patent is hereby corrected as shown below:

Title Page:
Item [75], Inventors, please delete "Ronnie C. Hanecak, San Clemente, CA (US); Kevin P. Anderson, Carlsbad, CA (US); Ming-Yi Chiang, San Diego, CA (US); Vickie L. Brown-Driver, Solana Beach, CA (US);";

Column 16, Claim 4, line 62, please delete "oligonueleotide" and insert therefore --oligonucleotide--;

Column 16, Claim 5, line 67, please delete "phosphorothioute" and insert therefore --phosphorothioate--;

Column 17, Claim 8, line 5, please delete "otigonucleotide" and insert therefore --oligonucleotide--;

Column 17, Claim 8, line 12, please delete "thionoalkyiphosphonate" and insert therefore --thionoalkylphosphonate--;

Column 17, Claim 8, line 25, please delete "$_{SO2}$CH" and insert therefore --$SO_2CH_3$--;

Column 17, Claim 8, line 36, please delete "6azo" and insert therefore --6-azo--;

Column 17, Claim 8, line 45, please delete "7-deazaudenine" and insert therefore --7-deazaadenine--;

Column 17, Claim 8, line 46, please delete "3-deazeadenine" and insert therefore --3-deazaadenine--;

Column 17, Claim 10, line 59, please delete "-O(CH$_2$ON(CH$_3$)$_2$" and insert therefore -- -O(CH$_2$)$_2$ON(CH$_3$)$_2$--;

Column 18, Claim 13, line 6, please delete "2" and insert therefore --2'--;

Column 18, Claim 15, line 9, please delete "otigonucleotide" and insert therefore --oligonucleotide--;

Column 18, Claim 15, line 9, please delete "4" and insert therefore --11--;

UNITED STATES PATENT AND TRADEMARK OFFICE
CERTIFICATE OF CORRECTION

PATENT NO. : 7,067,497 B2
APPLICATION NO. : 10/038335
DATED : June 27, 2006
INVENTOR(S) : C. Frank Bennett et al.

It is certified that error appears in the above-identified patent and that said Letters Patent is hereby corrected as shown below:

Column 18, Claim 15, line 16, please delete "thionoalkyiphosphonate" and insert therefore --thionoalkylphosphonate--;

Column 18, Claim 15, line 29, please delete "SO$_2$CH" and insert therefore --SO$_2$CH$_3$--;

Column 18, Claim 15, line 40, please delete "6azo" and insert therefore --6-azo--;

Column 18, Claim 15, line 49, please delete "7-deazaudenine" and insert therefore --7-deazaadenine--;

Column 18, Claim 15, line 50, please delete "3-deazeadenine" and insert therefore --3-deazaadenine--.

Signed and Sealed this

Seventh Day of November, 2006

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 13
<212> TYPE: DNA
<213> ORGANISM: Novel sequence
<220> FEATURE:
<223> OTHER INFORMATION: Antisense sequence

<400> SEQUENCE: 1
caguuagggu uag                                                         13

<210> SEQ ID NO 2
<211> LENGTH: 13
<212> TYPE: DNA
<213> ORGANISM: Novel sequence
<220> FEATURE:
<223> OTHER INFORMATION: Antisense sequence

<400> SEQUENCE: 2
cagttagggt tag                                                         13

<210> SEQ ID NO 3
<211> LENGTH: 14
<212> TYPE: DNA
<213> ORGANISM: Novel sequence
<220> FEATURE:
<223> OTHER INFORMATION: Antisense sequence

<400> SEQUENCE: 3
ttggggttgg ggtt                                                        14

<210> SEQ ID NO 4
<211> LENGTH: 24
<212> TYPE: DNA
<213> ORGANISM: Novel sequence
<220> FEATURE:
<223> OTHER INFORMATION: Antisense sequence

<400> SEQUENCE: 4
ttggggttgg ggttggggtt gggg                                             24

<210> SEQ ID NO 5
<211> LENGTH: 20
<212> TYPE: DNA
<213> ORGANISM: Novel sequence
<220> FEATURE:
```

-continued

```
<223> OTHER INFORMATION: Antisense sequence

<400> SEQUENCE: 5
gttggagacc ggggttgggg                                            20

<210> SEQ ID NO 6
<211> LENGTH: 20
<212> TYPE: DNA
<213> ORGANISM: Novel sequence
<220> FEATURE:
<223> OTHER INFORMATION: Antisense sequence

<400> SEQUENCE: 6
cacggggtcg ccgatgaacc                                            20

<210> SEQ ID NO 7
<211> LENGTH: 13
<212> TYPE: DNA
<213> ORGANISM: Novel sequence
<220> FEATURE:
<223> OTHER INFORMATION: Antisense sequence

<400> SEQUENCE: 7
caguuagaau uag                                                   13

<210> SEQ ID NO 8
<211> LENGTH: 13
<212> TYPE: DNA
<213> ORGANISM: Novel sequence
<220> FEATURE:
<223> OTHER INFORMATION: Antisense sequence

<400> SEQUENCE: 8
cagttagaat tag                                                   13

<210> SEQ ID NO 9
<211> LENGTH: 11
<212> TYPE: DNA
<213> ORGANISM: Novel sequence
<220> FEATURE:
<223> OTHER INFORMATION: Antisense sequence

<400> SEQUENCE: 9 tctaaccta a                                                      11

<210> SEQ ID NO 10
<211> LENGTH: 11
<212> TYPE: DNA
<213> ORGANISM: Novel sequence
<220> FEATURE:
<223> OTHER INFORMATION: Antisense sequence

<400> SEQUENCE: 10
tctaattcta a                                                     11
```